United States Patent [19]

Cricchio et al.

[11] 4,005,076
[45] Jan. 25, 1977

[54] HYDRAZONES OF 3-FORMYLRIFAMYCIN SV

[75] Inventors: Renato Cricchio, Via Carcano Varese; Giancarlo Lancini, Via Vittadini Pavia, both of Italy

[73] Assignee: Gruppo Lepetit S.p.A., Milan, Italy

[22] Filed: Dec. 30, 1974

[21] Appl. No.: 537,306

Related U.S. Application Data

[63] Continuation-in-part of Ser. No. 263,238, June 15, 1972, abandoned.

[30] Foreign Application Priority Data

June 24, 1971  Italy ............................. 89608/71

[52] U.S. Cl. .................. 260/239.3 P; 424/244; 424/263; 424/267; 424/250; 424/251; 424/258
[51] Int. Cl.$^2$ ..................................... C07D 498/08
[58] Field of Search ........................... 260/239.3 P

[56] References Cited

UNITED STATES PATENTS 3,342,810   9/1967   Maggi et al. ............... 260/239.3 P

FOREIGN PATENTS OR APPLICATIONS 1,109,631   4/1968   United Kingdom ......... 260/239.3 P

*Primary Examiner*—Henry R. Jiles
*Assistant Examiner*—Robert T. Bond
*Attorney, Agent, or Firm*—Theodore Post; C. Kenneth Bjork

[57] ABSTRACT

Hydrazones of 3-formylrifamycin SV of the general formula

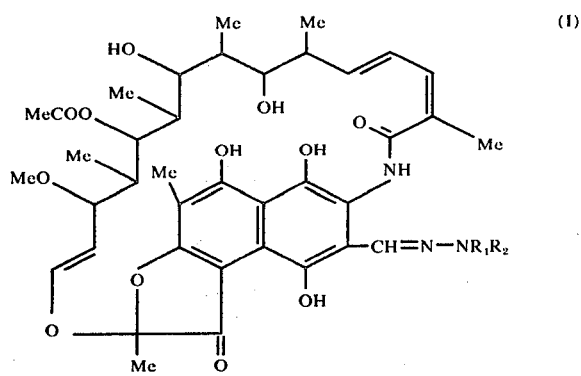

wherein $R_1$ is selected from the group hydrogen; alkyl; phenyl; and benzyl; $R_2$ is selected from the group alkyl; alkenyl; phenyl; and substituted phenyl; with the proviso that when $R_1$ is hydrogen or alkyl having 1 to 4 carbons, $R_2$ may not be phenyl; and the 16, 17; 18, 19; 28, 29-hexahydro and 27-demethoxy-27-hydroxy derivatives thereof.

11 Claims, No Drawings

HYDRAZONES OF 3-FORMYLRIFAMYCIN SV

CROSS REFERENCE TO RELATED APPLICATION

This application is a continuation-in-part of my copending application Ser. No. 263,238, filed June 15, 1972, now abandoned.

BACKGROUND OF THE INVENTION

The present invention is concerned with novel hydrazones of 3-formylrifamycin SV.

Certain hydrazones of 3-formylrifamycin SV are described in U.S. Pat. No. 3,342,810. These compounds, although possessing a good antibacterial activity, have practically no effect against bacteria which have become resistant to other rifamycins, namely, the well known and therapeutically useful 3-(4-methyl-1-piperazinyl-iminomethyl) rifamycin SV (rifampicin).

It is well known by those who are skilled in the antibiotic art that when a microorganism strain becomes resistant to a particular antibiotic, it is rather difficult to find another compound of the same antibiotic family which is capable of inhibiting the growth of said resistant mutant. In some instances, it is quite difficult to find compounds which are active against such a resistant strain even among other different species of antibiotics.

We have surprisingly found that representative compounds of this invention are able to inhibit at low concentration the growth of strains resistant to other rifamycins. In particular, compounds illustrative of the invention at concentrations of about 10 to 20 μg/ml or less inhibit the growth of a Staph. aureus Tour strain resistant to rifampicin.

SUMMARY OF THE INVENTION

The present invention is concerned with new derivatives of 3-formylrifamycin SV. More particularly the invention relates to hydrazones of 3-formylrifamycin SV of general formula

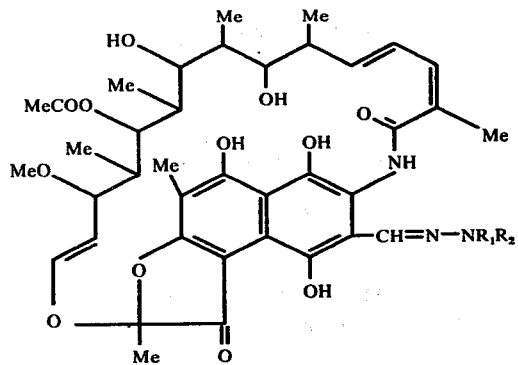

wherein
$R_1$ is selected from hydrogen; alkyl of 1 to 12 carbons; phenyl; and benzyl; $R_2$ is selected from alkyl of 5 to 12 carbons; alkenyl of 3 to 5 carbons; phenyl; phenyl substituted with one to three groups, each independently selected from lower alkyl, halo, nitro, lower alkoxy, trifluoromethyl, amino, sulfo, fluorosulfonyl, lower alkylsulfonyl and fluoro-lower alkylsulfonyl; and phenoxy-lower alkyl, wherein the lower alkyl moiety has 2 to 4 carbons and the phenoxy group may optionally have one to three substituents, each independently selected from halo, amino, and acetamino; 5 to 15 membered cycloalkyl; 4-biphenyl; 4-phenylbenzyl; a heterocyclic ring selected from pyridine, pyridine substituted with 1 to 2 groups, each independently selected from lower alkyl and nitro, N-lower alkyl-substituted piperidine, pyrimidine, pyrimidine substituted with 1 to 2 groups each independently selected from lower alkyl, hydroxy and nitro, pyridazine, pyridazine substituted with 1 to 2 groups, each independently selected from amino, chloro, phenoxy, piperidino, N-lower alkyl-piperazino, and bis-(hydroxyethyl)amino, quinoline, quinoline substituted with 1 to 2 groups each independently selected from lower alkyl, lower alkoxy, fluoro, trifluoromethyl and phenyl; with the proviso that when $R_1$ is hydrogen or alkyl having 1 to 4 carbons, $R_2$ may not be phenyl; and the 16, 17; 18, 19; 28, 29-hexahydro and 27-demethoxy-27-hydroxy derivatives thereof.

In the specification and claims, the term "alkyl having 1 to 12 carbons" designates a straight or a branched aliphatic radical such as, for example, methyl, ethyl, propyl, butyl, isobutyl, amyl, isoamyl, octyl or dodecyl; the term "alkenyl having 3 to 5 carbons" designates an aliphatic radical having from 3 to 5 carbons and one ethylenic unsaturation in the chain such as, for example, allyl, 2-isobutenyl or 2-pentenyl; the term and moiety "lower alkyl", where not expressly defined otherwise, designates a straight or branched chain aliphatic radical having 1 to 4 carbons such as, for example, methyl, ethyl, propyl, butyl or tert-butyl; the term "lower alkoxy" designates an alkoxy group wherein the aliphatic portion has 1 to 4 carbons; the term "halo" designates chloro, bromo or fluoro; the term "5 to 15 carbon cycloalkyl" designates a radical derived from an alicyclic ring such as for example, cyclopentyl, cyclohexyl, cycloheptyl, cyclooctyl, cyclopentadecyl and adamantanyl.

In addition to being active against bacteria which have become resistant to other rifamycins, the inventive compounds are also active against the usual Gram positive and Gram negative bacteria. In particular, the new compounds show a remarkable activity against Staphylococcus aureus, Streptococcus faec., Streptococcus hemoliticus and Diplococcus pneumoniae strains. In these cases the minimum inhibiting concentration ranges from about 0.001 to about 0.5 μg/ml.

Another very important feature of the inventive compounds is their inhibiting activity of DNA-polymerases which are characteristic of human leukemic blood lymphoblasts and against typical nucleotidyl transferases (polymerases) of virus not utilized by the normal cell.

DESCRIPTION OF THE PREFERRED EMBODIMENTS

To prepare the compounds of this invention, 3-formylrifamycin SV or the corresponding 16, 17; 18, 19; 28, 29-hexahydro compound is condensed in an organic solvent medium with a stoichiometric proportion of a hydrazine of the formula $H_2N-NR_1R_2$ wherein $R_1$ and $R_2$ have the above-given significance.

After standing at room temperature for a period of time varying from 10 minutes to several hours, the crude compound is recovered by concentrating or evaporating the solvent. The purification of these compounds does not represent a particular problem for those skilled in the field of organic chemistry and is generally effected by crystallization from a suitable solvent which, for example, may be selected from 1 to 4 carbon alkanols, 2 to 4 carbon acyl esters of 1 to 4 carbon alkanols or benzene. As appears from the generic formula of the inventive compounds, a large number of derivatives falling within the scope of the invention can be synthetized by selecting appropriate hydrazine moieties. In some instances when the hydrazine contains a strongly acidic group such as sulfo, the final rifamycin derivative may be hydrolized in the 27-position to the corresponding 27-demethoxy-27-hydroxy compound during the hydrazone formation.

The following additional description and examples further describe the invention and the manner and process of making and using it to enable the art skilled to make and use the same and set forth the best mode contemplated by the inventors of carrying out the invention.

GENERAL METHOD OF PREPARATION OF THE HYDRAZONES

To a tetrahydrofurane solution of a 0.01 molar proportion of 3-formylrifamycin SV or the corresponding hexahydro compound, 0.01 molar proportion of a hydrazine, as characterized above, is added at room temperature with stirring. After agitation for a period of time varying from about 10 minutes to about 3 hours, a drop of the solution is tested by thin layer chromatography on silica gel to determine the disappearance of the starting 3-formylrifamycin SV compound and the formation of the end product.

After complete disappearance of the carbonyl starting compound, the solution is concentrated to dryness and the crude product is recovered and purified by crystallization from a solvent or by column chromatography.

In following Table 1, the chemical-physical data of some representative hydrazones of formula (I) are given. These are prepared by reacting 3-formylrifamycin SV and the corresponding hydrazine, following the procedure set forth directly hereinbefore. The term "hexahydro" indicates that the specific compound has been prepared from the corresponding 3-formyl-hexahydrorifamycin SV.

TABLE 1

| Example No. | $R_1$ | $R_2$ | Crystallization or Chromatographic Solvent | Yield % | M.P. °C. | λmax | Significant U.V. and Visible Bands $E_{1cm}^{1\%}$ |
|---|---|---|---|---|---|---|---|
| 1 | H | (cyclohexenyl-H) | column CHCl$_3$/MeOH | 48 | 157–159 | 475 331 | 170.6 281.9 |
| 2 | H | (cyclohexyl-H) | column CHCl$_3$/MeOH | 47 | 157–159 | 475 330 | 178.5 290.0 |
| 3 | CH$_3$ | C$_5$H$_{11}$ | methanol | 70 | 150–153 | 480 343 | 130 235 |
| 4 | H | C$_{12}$H$_{25}$ | ethyl acetate/ ligroin | 80 | 122–123 | 480 340 | 139 252 |
| 5 | H | (pyridazinyl-N-piperazinyl-CH$_3$) | EtOAc | 56 | 200 dec. | 491 356 | 180.5 291.0 |
| 6 | H | (pyridazinyl-N-piperidinyl) | Benzene | 35 | 210 dec. | 485 352 | 165.9 258.3 |
| 7 | H | (pyrimidinyl-CH$_3$, OH) | Methanol | 68 | 200 dec. | 483 343 | 191.6 341.3 |
| 8 | H | (pyridazinyl-OC$_6$H$_5$) | Benzene | 81 | 188–190 | 485 348 | 164.3 326.8 |
| 9 | H | (piperidinyl-N-CH$_3$) | EtOAc ethyl acetate | 60 | 180 dec. | 473 332 | 166.0 275.0 |
| 10 | H | (pyridazinyl) | Methanol | 60 | 208–210 | 480 345 | 191.4 344.0 |
| 11 | (phenyl) | (phenyl) | MeOH | 48 | 168–172 | 486 360 | 185.8 238.9 |

TABLE 1-continued

| Example No. | R₁ | R₂ | Crystallization or Chromatographic Solvent | Yield % | M.P. ° C. | λmax | Significant U.V. and Visible Bands $E^{1\%}_{1cm}$ |
|---|---|---|---|---|---|---|---|
| 12 | H | 2,5-dinitro-4-methylphenyl | column CHCl₃/MeOH | 42 | 205–215 dec. | 500 390 | 200.5 279.3 |
| 13 | H | cycloheptyl (with H) | column CHCl₃/MeOH | 52 | 157–159 | 475 330 | 173.0 274.0 |
| 14 | H | cyclooctyl (with H) | column CHCl₃/MeOH | 46 | 152–156 | 476 335 | 175.0 282.3 |
| 15 | phenyl | benzyl (—CH₂—C₆H₅) | column CHCl₃/MeOH | 60 | 150–151 | 490 363 | 173.2 231.2 |
| 16 | H | (polycyclic structure with H) | column CHCl₃/MeOH | 40 | 140 | 483 343 | 135.4 240.9 |
| 17 | H | 2,4,6-trimethylquinolin-?-yl | ethyl acetate | 75 | 206 dec. | 510 383 | 166.0 297.0 |
| 18 | H | 2,4-dimethylquinolin-?-yl | Methanol | 75 | 193 dec. | 504 364 | 194.0 246.0 |
| 19 | H | 2,4-dimethyl-8-methoxyquinolin-?-yl | ethyl acetate | 75 | 212 dec. | 512 382 325 | 170.0 283.0 178.0 |
| 20 | H | 2,4-dimethylquinolin-?-yl | ethyl acetate | 65 | 208 dec. | 512 383 | 167.0 304.0 |
| 21 | H | 4,6-dimethylpyrimidin-?-yl | Methanol | 55 | 215 dec. | 487 348 | 191.6 382.8 |
| 22 | H | 4-methyl-8-trifluoromethylquinolin-?-yl | Benzene | 45 | 185 dec. | 500 384 | 149.1 249.5 |
| 23 | H | 2-phenyl-4-methyl-7-trifluoromethylquinolin-?-yl | Benzene | 40 | 185 dec. | 508 389 | 134.2 190.0 |

TABLE 1-continued

| Example No. | R₁ | R₂ | Crystallization or Chromatographic Solvent | Yield % | M.P. °C. | Significant U.V. and Visible Bands λmax | $E^{1\%}_{1cm}$ |
|---|---|---|---|---|---|---|---|
| 24 | H | 6-fluoro-4-methylquinolin-2-yl | ethyl acetate | 50 | 200 dec. | 502 / 384 | 161.2 / 259.2 |
| 25 | H | 4,8-dimethylquinolin-2-yl | Methanol | 50 | 193–194 | 502 / 368 | 157.8 / 248.7 |
| 26 | H | 3-methylphenyl | Carbon tetrachloride | 90 | 178–180 | 485 / 358 | 237.5 / 243.8 |
| 27 | CH₃ | 2,4-dinitrophenyl | Methanol | 90 | 220–224 | 525 / 425 / 340 | 210.0 / 235.0 / 228.0 |
| 28 | H | —CH₂—CH=CH₂ | Methanol | 40 | 170–175 | 475 / 332 | 160.5 / 272.1 |
| 29 | H | —CH₂—CH₂—O—phenyl | ethyl acetate/ligroin | 75 | 145–148 | 470 / 331 | 135.0 / 233.0 |
| 30 | H | 4-nitrophenyl | Methanol | 85 | 214–216 | 501 / 440 / 348 | 326.9 / 326.9 / 186.5 |
| 31 | H | 2,4-dinitrophenyl; 16,17;18,19;28,29 hexahydro | column chloroform:methanol 96:4 ethyl acetate/light petroleum | 55 | 120–124 dec. | 502 / 401 | 143.3 / 215.9 |
| 32 | H | 4-sulfophenyl; 27-demethoxy-27-hydroxy | ethyl acetate | 50 | 250 dec. | 475 / 358 | 179.4 / 268.1 |
| 33 | H | 2-methoxyphenyl | Methanol | 75 | 165–169 | 480 / 360 | 230.7 / 225.1 |
| 34 | H | 4-amino-2,6-dichlorophenoxyethyl | Carbon tetrachloride | 95 | 160–163 | 474 / 333 | 154.5 / 244.4 |
| 35 | H | 2-nitrophenyl | ethyl acetate | 85 | 244–246 | 348 | 187.7 / 225.5 |

TABLE 1-continued

| Example No. | R₁ | R₂ | Crystallization or Chromatographic Solvent | Yield % | M.P. °C | Significant U.V. and Visible Bands λmax | $E_{1cm}^{1\%}$ |
|---|---|---|---|---|---|---|---|
| 36 | H | (3-NO₂-phenyl) | Carbon tetrachloride | 70 | 200–203 | 490 357 | 204.0 284.0 |
| 37 | H | (4-F-phenyl) | Methanol | 80 | 190–193 | 485 358 | 222.0 233.0 |
| 38 | H | (2-CH₃-phenyl) | Carbon tetrachloride/ligroin | 85 | 160–164 | 484 357 | 203.0 226.0 |
| 39 | H | (2,4,5-trichlorophenyl) | Methanol | 90 | 174–176 | 485 342 | 156.8 250.8 |
| 40 | H | (4-SO₂F-phenyl) | Carbon tetrachloride | 72 | 182–187 | 500 365 | 151 265 |
| 41 | H | (3-SO₂F-4-CH₃-5-C(CH₃)₃-phenyl) | Carbon tetrachloride/ligroin | 63 | 136–147 | 475 336 | 138 232 |
| 42 | CH₃ | —CH₂—(4-biphenylyl) | Methanol | 75 | 180–184 (dec.) | 485 344 | 138.4 280.6 |

Following the same general procedure as set forth for the foregoing Examples, the following hydrazone compounds were similarly prepared.

EXAMPLE 43

3-Formylrifamycin SV: hydrazone of ((3-trifluoromethyl)-phenyl) hydrazine was prepared by reacting 3-formylrifamycin SV with ((3-trifluoromethyl)-phenyl) hydrazine. The hydrazone product was a red solid which melted with decomposition at 178°–181° C. The structure was confirmed by NMR.

EXAMPLE 44

3-Formylrifamycin SV: hydrazone of (4-((difluoromethyl)sulfonyl)phenyl) hydrazine was prepared by reacting 3-formylrifamycin SV with (4-((difluoromethyl)sulfonyl)phenyl)hydrazine. The hydrazone product was a red solid which melted with decomposition at 194°–197° C. The structure was confirmed by NMR.

EXAMPLE 45

3-Formylrifamycin SV: hydrazone of (2,4-bis-(methylsulfonyl)phenyl) hydrazine was prepared by reacting 3-formylrifamycin SV with (2,4-bis(methylsulfonyl)phenyl) hydrazine. The hydrazone product was a red powder which melted with decomposition at 196°–198° C. The structure was confirmed by NMR.

EXAMPLES 46 AND 47

In a similar manner to the foregoing, there also were prepared the hydrazones of 3-formylrifamycin SV with N,N-diamylhydrazine (dec. at 113° C.) and with 1-adamantanylhydrazine (m.p. 160° C. with decomposition).

The compounds listed in the foregoing Examples are given by way of illustration only, it being intended that other hydrazones falling within the generic formula are also useful for the purposes which have been explained. For example, other hydrazones are advantageously prepared by the same procedures starting from 3-formylrifamycin SV and hydrazines of the formula NH₂—NR₁R₂ as set forth in the following Table 2.

TABLE 2

| Example No. | R₁ | R₂ |
|---|---|---|
| 48 | H | 6-bis—(hydroxyethyl)—amino-3-pyridazinyl |
| 49 | C₄H₉ | cyclohexyl |
| 50 | H | 2-phenyl-6-methoxy-4-quinolyl |

TABLE 2-continued

| Example No. | $R_1$ | $R_2$ |
|---|---|---|
| 51 | $C_2H_5$ | $-(CH_2)_{11}-CH_3$ |
| 52 | H | $-C_6H_4-SO_2CH_3-4$ |
| 53 | H | $-C_6H_3(NO_2-2) (SO_2F-4)$ |
| 54 | $C_5H_9$ | $C_nH_{17}$ |
| 55 | isoamyl | $CH_2CH:CHCH_2CH_3$ |
| 56 | $CH_3$ | m-nitrophenyl |
| 57 | H | p-chlorophenyl |
| 58 | H | p-bromophenyl |
| 59 | H | m-fluorophenyl |
| 60 | H | 2,5-difluorophenyl |
| 61 | H | $C_6H_3(SO_2F)_2-2,6$ |
| 62 | H | p-tolyl |
| 63 | H | 4-biphenylyl |
| 64 | H | o-trifluoromethylphenyl |
| 65 | H | 2-(2,6-dibromo-4-amino phenoxy)-ethyl |
| 66 | H | 2-(2,6-dibromo-4-acetamido phenoxy)-ethyl |
| 67 | H | 4-phenylbenzyl |
| 68 | H | 2-pyridyl |
| 69 | H | 2-isobutenyl |
| 70 | H | $C_6H_4SO_2CF_3-4$ |
| 71 | H | 2,4,6-trinitrophenyl |
| 72 | H | 4-amino-6-chloro-3-pyridazinyl |
| 73 | H | 5-nitro-2-pyrimidyl |
| 74 | benzyl | benzyl |
| 75 | H | 3-methyl-5-nitro-2-pyridyl |

One of the most important characteristics of the new hydrazones is their activity against rifampicin-resistant *Staphylococcus aureus* strains. Rifampicin, that is 3-(4-methyl-1-piperazinyl)iminomethylrifamycin SV, disclosed in U.S. Pat. No. 3,342,810, is the most known and widely used rifamycin derivative in therapeutic practice.

The following table illustrates the results in vitro against a *Staphylococcus aureus* strain which is resistant to rifampicin (i.e. rifampicin does not inhibit its growth even at a concentration higher than 100 μg/ml.). The data of the new compounds are compared with those of representative hydrazones disclosed in U.S. Pat. No. 3,342,810.

TABLE 3

| No. of Example | Minimal inhibitory concentration μg/ml. | No. of Example | Minimal inhibitory concentration μg/ml. |
|---|---|---|---|
| 1 | 20 | 33 | 50 |
| 2 | 20 | 34 | 50 |
| 3 | 10 | 35 | 20 |
| 11 | 2 | 36 | 50 |
| 12 | 10 | 37 | 50 |
| 13 | 10 | 38 | 20 |
| 14 | 5 | 39 | 5 |
| 15 | 2 | 41 | 20 |
| 22 | 50 | 42 | 5 |
| 23 | 20 | 43 | 10 |
| 25 | 20 | 46 | 1 |
| 26 | 20 | 47 | 5 |
| 3-(4-Methyl-1-piperazinyl)iminomethyl-rifamycin SV | | | >100 |
| p-Carboxyphenylhydrazone of 3-formylrifamycin SV | | | >100 |
| N-Methylhydrazone of 3-formylrifamycin SV | | | >100 |
| N,N-Diethylhydrazone of 3-formylrifamycin SV | | | >100 |
| Phenylhydrazone of 3-formylrifamycin SV | | | 100 |

It is known from studies on representative members of virus groups that they either carry or induce in host cells polymerases as an essential part of their replication. Thus, there are viruses such as picornoviruses or polioviruses which induce RNA-dependent RNA-polymerase while other groups such as leukemia-sarcoma viruses carry an RNA-dependent DNA-polymerase. The presence and the very important role of the RNA-dependent DNA-polymerase reverse transcriptase in oncogenic RNA viruses has been discovered by D. Baltimore, Nature, 226, 1209 (1970) and by H. M. Temin et al., Nature, 226, 1211 (1970). Recent discovery of RNA-dependent DNA-polymerase enzyme in RNA tumor viruses of animal species has been confirmed also by other authors, as described in the papers hereinbelow listed:

Green et al.: Mechanism of carcinogenesis by RNA tumor viruses. I. An RNA-dependent DNA-polymerase in murine sarcoma viruses. Proc. Nat. Acad. Sci. USA 67: 385-393, 1970.

Spiegelman et al.: Characterization of the products of RNA-directed DNA-polymerase in oncogenic RNA viruses, Nature, London, 227: 563, 1970.

Hatanaka et al.: DNA polymerase activity associated with RNA tumor viruses. Proc. Nat. Acad. Sci. USA 67: 143, 1970.

Scolnick et al.: DNA synthesis by RNA containing tumor viruses. Proc. Nat. Acad. Sci. USA 67: 1034, 1970.

RNA virus implication in some tumors has been supported also by other facts:

Reverse transcriptase has been found to be present in particles from human milk obtained from women with a known history of breast cancer and from inbred population. (Scholn et al., Nature, 231, 97, 1971).

Priori et al. (Nature New Biology, 232, 16, 1971) isolated a virus named ESP-1 containing reverse transcriptase from cells from the pleural fluid of a child with lymphoma and have successfully grown it in tissue cultures.

The presence in human breast cancer of RNA homologous to mouse mammary tumor virus RNA has been demonstrated through molecular hybridation experiments by R. Axel et al. (Nature, 235, 32, 1972).

At present there are no very effective drugs for treating viral diseases since viruses and cells have common metabolic requirements and pathways. The most promising approach to viral chemotherapy clearly is the design of suitable chemicals which combine specifically with viral or virus transformed cell polymerases but not with host cell polymerases controlling the expression of genetic information of viruses. Specific inhibitors of the viral or virus transformed cell enzymes and, in particular, inhibitors of polymerases of RNA tumor viruses may have an important role in providing drugs for leukemia and other cancer therapy.

The inhibiting activity of the inventive compounds has been tested on RNA-dependent DNA polymerase of murine sarcoma virus (endogenous) and RNA-dependent DNA polymerase activity of purified enzymes. The inhibition was tested according to the methods described by C. Gurgo et al., Nature, New Biology, 229, 111, 1971. The effect of different concentrations of drugs on polymerase activity was determined by following $^3$H-dTTP (tritiated thymine deoxyriboside triphosphate) incorporation into the insoluble fraction. A typical example of the experimental procedures is the following.

Isolation of Virus and Purification of Viral Polymerase

Virus was isolated and purified from murine sarcoma virus (Moloney isolate) transformed rat cells (78A1 cells) and murine sarcoma virus (Harvey isolate) transformed mouse cells (MEH cells) as previously described (Green et al., Proc. Nat. Acad. Sci. USA 67, 385–393, 1970, Rokutanda et al., Nature, 227, 1026–1028, 1970). The virion polymerase was purified 20–40 fold by incubation of purified virus with 0.5% NP-40 (nonidet P-40) in 0.1 M NaCl, 0.01 M Tris buffer (pH 7.6), 0.001 M EDTA for 5 minutes at room temperature and zonal centrifugation in 15–30% sucrose gradients in 10 mM sodium phosphate buffer (pH 7.4), 2.5 mM MgCl$_2$, 10 mM dithiothreitol, and 5% glycerol for 24 hours at 38,000 rpm in a Spinco SW41 rotor. The peak fractions of enzyme activity (13–17) of 22 fractions collected, were pooled and stored at −70° C. in 30% glycerol.

DNA Polymerase Assay

Enzyme incubation was performed for 1 hour at 37° C. in 100 $\mu$l of reaction mixture containing 40 mM Tris buffer (pH 8.0), 5 mM dithiothreitol, 30 mM NaCl, 2.5 mM MgCl$_2$, 0.1 mM dATP, dGTP, dCTP, and 10 $\mu$Ci of $^3$H-dTTP (12–18 Ci/mmole) as described by Green et al. in Proc. Nat. Acad. Sci. USA 67, 385–393, 1970. The reaction was terminated by the addition of 150 $\mu$l of 1N perchloric acid. Calf thymus DNA (100 $\mu$g) was added as carrier; the radioactive DNA product was processed as described in the two papers mentioned above. Endogenous RNA-dependent DNA-polymerase activity was measured after the addition of 0.01% NP-40 to purified virus at the time of assay. The DNA-polymerase activity of purified viral polymerase was measured with 2 $\mu$g of poly d (A-T) as template and no NP-40.

Test for Inhibition by Rifamycin Derivatives of this Invention

Rifamycin derivatives of this invention were dissolved in dimethylsulfoxide (DMSO) at a concentration of 5 mg/ml and stored at 4° C. Inhibition of the endogenous RNA-dependent DNA-polymerase activity was tested by adding 2 $\mu$l of derivative appropriately diluted in DMSO or 2 $\mu$l of DMSO (control) to the assay mixture prior to addition to disrupted virus which contained 15 to 30 $\mu$g of viral protein. Enzyme incubation was performed for 60 minutes at 37° C. Inhibition of purified enzyme was tested by pre-incubation of 2 $\mu$l of derivative or DMSO with 30 $\mu$l of enzyme (1 to 2 $\mu$g of protein) for 10 minutes at 37° C.; then 70 $\mu$l of substrate mixture were added and the mixture further incubated and processed as described above.

In representative tests, the inventive compounds described in Examples 11, 12, 13, 14, 15 and 16 at a concentration of 2–100 $\mu$g/ml or less reduced the incorporation of H$^3$-dTTP to less than 10 percent of that found in the control tests, clearly demonstrating inhibition of mechanism of carcinogenesis by RNA tumor viruses, according to the most recent biochemical points of view.

The inhibiting effect of reverse transcriptase has been confirmed also by test of polymerase from murine leukemia virus. Murine leukemia virus RNA-polymerase was prepared from Triton X 100 disrupted virions, as described by Gallo et al. in Nature, New Biology, 232, 141, (1971). Virus of both Rauscher and Moloney types were previously purified by banding in the 1.16 g/ml. region of a sucrose density gradient after initial low speed centrifugation to remove cellular debris and cushioning of 60% sucrose through 20% sucrose. Final concentration of virus preparation was at 10$^{11}$ particles/ml. As template endogenous 70 S RNA was used. Concentrations of 50 $\mu$g/ml. or less of representative compounds of this invention were found to be effective in inhibiting the enzyme. For instance, inhibitions of about 50 percent were obtained with concentrations of only about 5 $\mu$g/ml. of representative compounds. Similar results were found by using tumor cell polymerases of human origin. In this case the inhibiting activity was studied also on normal cell polymerases to characterize a selective effect. Representative rifamycin derivatives of formula I have been evaluated for their effects on two purified DNA polymerases isolated from (1) human normal (PHA stimulated) blood lymphocytes (2) a lymphoblast cell line (derived from a normal donor) and (3) human leukemic blood lymphoblast. Synthetic and/or native templates were used.

A typical example of the experimental procedure is the following.

Human Blood Lymphoblasts

Leukemic lymphoblasts were isolated from the peripheral blood of patients with acute lymphocytic leukemia (ALL) by leukophoresis. The cells were washed and erythrocytes removed by hypotonic lysis. Normal lymphocytes were obtained from the peripheral blood from healthy donors after removal of granulocytes by nylon column chromatography. They were stimulated with phytohemagglutinin (PHA) for 72 hours as described before (Gallo et al., Nature, 228, 927, 1970; Gallo et al., Science, 165, 400, 1968) in order to maximize DNA polymerase activity.

However, because of the logistic problems in obtaining sufficient amounts of these cells, a human "normal" tissue culture cell line (1788) was used to supply less purified DNA polymerases for some of the initial survey studies. Compounds of interest were then studied in more detail with the more purified enzymes from the normal and leukemic blood lymphocytes. These tissue culture cells were obtained from Associated Biomedic Systems, Inc.

DNA Polymerase Preparations

Cellular DNA polymerases were extracted and purified from normal blood (PHA stimulated) lymphocytes, and leukemic blood lymphocytes and 1788 lymphoid cells by homogenization in hypotonic buffer followed by Triton X 100 and/or high salt extraction of the extralysosomal pellet. After differential centrifugation, cellular extracts were further purified by DEAE cellulose, phosphocellulose, and Sephadex G 200 column chromatography.

DNA Polymerase Assays

DNA polymerase assays were carried out in a final volume of 100 μl. The assay mixture contained Tris-HCl buffer, pH 8.3, 50 mM; MgAc, 6.0 mM; dithiothreitol, 8.0 mM; NaCl, 60 mM. Adjustment of pH was carried out after addition of inhibitors which were previously dissolved in dimethylsulfoxide (DMSO). The final concentration of DMSO was 0.5% and all control samples included this amount of DMSO. An enzyme concentration that catalyzes an incorporation of approximately 1.0 pmole/hr was used in the assay. The enzyme was in most cases preincubated for 5 minutes with the inhibitor. The reaction was then initiated by the addition of template either synthetic DNA (poly d(AT) Miles Lab.) and DNA.RNA hybrid (oligo dT.poly rA), at 5 μg/ml., or native templates: activated salmon sperm DNA at 50 μg/ml., and endogenous 70S viral RNA; 10 μCi of ($^3$H-methyl)-TTP (New England Nuclear, 18.6 mCi/μmole lyophilized and redissolved in 0.01 M HCl just prior to usage) and dATP (8 × $10^{-5}$M, with synthetic template) or all three deoxynucleoside triphosphates (8 × $10^{-5}$M with RNA or DNA templated reactions). In some experiments, there was no preincubation of enzyme with inhibitor.

In these cases, reactions were initiated by adding enzyme to the complete reaction mixture, which included the inhibitor. Samples were withdrawn at the start of incubation and after 30 minutes, and terminated by the addition of 2 ml. of 0.08 M sodium pyrophosphate, and precipitated in 12.5% cold trichloroacetic acid (TCA) with yeast RNA (400 μg) as carrier. The products were collected on Millipore filter, washed extensively with 5% TCA and 1 ml. of DMSO-ethanol 0.1 M NaCl mixture (0.5:70:29.5), dried and counted in 2 ml. of BBS$_3$ (Beckman) and 10 ml. of liquifluor (New England Nuclear) in a Packard liquid scintillation counter.

In representative experiments, concentrations varying from 5 to 10 μg/ml. of compounds of Examples 11 and 12 were found to provoke a 50% inhibition of leukemic polymerase with a synthetic DNA template. Reactions templated by a synthetic RNA template (poly rA.rU) were even more susceptible.

Representative experiments carried out with native template on normal and tumor cell polymerases showed a higher susceptibility of the tumor enzymes to the tested compounds. For instance, a concentration of about 5 μg/ml of compound 12 gives a 44 percent inhibition of tumor virus polymerases while it is practically inactive on normal polymerases. Also the compound of Example 16 is specifically active against tumor virus polymerase at a concentration of 10 μg/ml.

The following table shows the effect of some rifamycins and of the compounds of Examples 12 and 16 against sarcoma virus DNA-polymerases (SSV-DNA-P) and polymerases of normal cell, i.e. mouse embryo DNA-polymerase I (ME-DNA-P$_1$), mouse embryo DNA-polymerase II (ME-DNA-P$_2$), mouse embryo RNA-polymerase I (ME-RNA-P$_1$) and mouse embryo RNA-polymerase II (ME-RNA-P$_2$).

TABLE 4

Effect of Rifamycins and 3-Substituted Rifamycins on Activity of SSV-Polymerase and Mouse Embroy Cell Polymerases

| Compound | SSV-DNA-P at | | | ME-DNA-P$_1$ at | | | % Control Activity of ME-DNA-P$_2$ at | | | ME-RNA-P$_1$ at | | ME-RNA-P$_2$ at | |
|---|---|---|---|---|---|---|---|---|---|---|---|---|---|
| | 5μg | 10μg | 100μg | 5μg | 10μg | 100μg | 5μg | 10μg | 100μg | 10μg | 100μg | 5μg 10μg | 100μg |
| rifamycin B | 96 | 104 | 75 | | 103 | 81 | | 46 | 4 | 76 | 85 | 102 | 95 |
| rifamycin O | 100 | 98 | 83 | | 92 | 65 | | 97 | 5 | 77 | 75 | 93 | 65 |
| rifamycin S | 88 | 108 | 100 | | 84 | 86 | | 94 | 9 | 102 | 90 | 78 | 81 |
| rifamycin SV | 105 | 75 | 61 | 91 | 95 | 105 | 94 | 100 | 72 | 84 | 106 | 89 87 | 82 |
| Rifampicin i.e. Rifamycin SV | 94 | 97 | 96 | | 99 | 56 | | 96 | 16 | 77.7 | 86 | 81 | 99 |

| Example 12, i.e. rifamycin SV | 44 | 34 | 1 | 102 | 83 | 11 | 72 | 83 | 46 | 115 | 100 | 92 | 72 |

| Example 16, i.e. rifamycin SV | 84 | 41 | 1 | 98.3 | 110 | 6.4 | 121 | 91.1 | 14.6 | 103 | 82 | 103 96 | 83 |

Templates used in the Enzymatic Assays were the following: SSV-DNA-P: Oligo dT.Poly rA. ME-DNA-P$_1$ and ME-DNA-P$_2$: activated Calf-Thymus DNA. Me-RNA-P$_1$ and ME-RNA-P$_2$: Single Stranded Calf-Thymus DNA.

Other biological characteristics of the new rifamycin derivatives include inhibition of focus formation on mouse, rat and human cells by the Moloney and Kirsten strain of murine sarcoma virus; selective inhibition of virus production by already transformed mouse and human cells; detection of revertant cells using the murine sarcoma virus transformed non-producer mouse and rat cell systems. The hydrazone compounds of the present invention have moreover confirmed their selective toxicity for virus transformed cells of mouse, rat and human origin when tested for colony forming ability.

In studies to determine the effect of the compounds in inhibiting focus formation by Moloney sarcoma virus on BALB/3T3 tissue cultures the following procedure is employed.

BALB/3T3 cell cultures are grown in 250 ml. plastic flasks in growth medium consisting of Eagle's minimal essential medium with 10% fetal bovine serum. Cell counts are made with a Coulter counter after suspending the cells with trypsin-EDTA and diluting in growth medium. Moloney murine sarcoma virus, as a tumor homogenate is employed. It is passaged four times in a Swiss-derived high passage mouse embryo cell line and assayed for focus-forming units in BALB/3T3 cells. In conducting the studies, a modification of the method described by Hartley and Rowe, Proc. Nat. Acad. Sci. 55, 780 (1966) is used. In the present work, flasks are seeded with from 1–2 × 10⁶ cells in 25 ml. of growth medium and incubated at 37° C. for 24 hours. Following the removal of fluids, virus at a predetermined number of focus forming units is introduced into 0.5 ml. of growth medium and allowed to absorb on the monolayer of cells for 90 minutes at 37° C. Following this adsorption period, a predetermined quantity, usually at a dose rate of from about 5 to 10 μg/ml. of a rifamycin compound (previously dissolved in dimethyl-sulfoxide at a concentration of 1 mg/ml) and carried in 25 ml. of growth medium, is added and the cultures returned to the incubator. As a control, dimethylsulfoxide alone in the growth medium is added to a separate culture. After three day's inoculation, the cultures are fluid-changed and foci of transformed cells counted at day seven.

In this same method, vesicular stomatitis virus, New Jersey serotype is studied. Methods used to grow and assay this virus have been described by Hackett et al., Virology, 31, 114 (1967). These properties indicate that these compounds possess an effective inhibitory activity on virus induced tumors in animals.

The starting compound for preparing hexahydro derivatives of the rifamycins of formula I, i.e., 16, 17; 18, 19; 28, 29-hexahydro-3-formylrifamycin SV is obtained in the following way.

Twenty grams of rifamycin S suspended in 600 ml. of dry ethanol is hydrogenated in a Parr bomb with 2 g. of PtO₂ as the catalyst for 3 hours at room temperature under a hydrogen pressure of about 5 atmospheres. After filtering off the catalyst, the solution is evaporated to dryness and the crude product dissolved in tetrahydrofuran is maintained under stirring with 18 g. of MnO₂ at room temperature. The inorganic precipitate is filtered off and after concentration of the filtrate to a small volume, the mixture is taken up with ethyl acetate (300 ml.) and washed with water. The organic layer is dried over Na₂SO₄ and after evaporation gives 8 g. of hexahydrorifamycin, m.p. 158°–160° C. (from methanol). The product is then converted into the corresponding 3-formyl derivative by following essentially the same method described in Example 5 of British Patent 1,219,360. The crude product may be purified by column chromatography of its chloroform solution through silica gel and by eluting with chloroform containing 1% of methanol. The compound recovered by evaporation of the chromatographed solution is 16, 17; 18, 19; 28, 29-hexahydro-3-formylrifamycin SV, melting at 126°–133° C.

We claim:
1. A compound of the formula

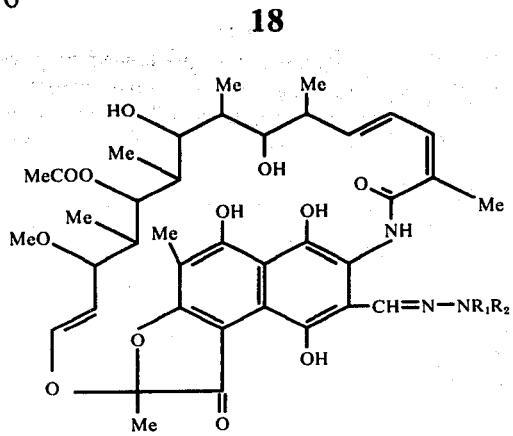

wherein
R₁ is selected from hydrogen, 1 to 12 carbon alkyl, phenyl and benzyl; R₂ is selected from 5 to 12 carbon alkyl; 3 to 5 carbon alkenyl; phenyl; phenyl substituted with one to three groups each independently selected from lower alkyl, halo, nitro, lower alkoxy, trifluoromethyl, amino, sulfo, fluorosulfonyl, lower alkylsulfonyl and fluoro-lower alkylsulfonyl; phenoxy-lower alkyl wherein the lower alkyl moiety has 2 to 4 carbons and the phenoxy group may have one to three substituents each independently selected from halo, amino, and acetamino; 5 to 15 carbon cycloalkyl; 4-biphenyl; 4-phenylbenzyl; heterocyclic ring selected from pyridine, pyridine substituted with 1 to 2 groups each independently selected from lower alkyl and nitro, N-lower alkyl-substituted piperidine, pyrimidine, pyrimidine substituted with 1 to 2 groups, each independently selected from lower alkyl, hydroxy and nitro, pyridazine, pyridazine substituted with 1 to 2 groups each independently selected from amino, chloro, phenoxy, piperidino, N-lower alkyl-piperazino and bis(hydroxyethyl)amino, quinoline, quinoline substituted with 1 to 2 groups each independently selected from lower alkyl, lower alkoxy, fluoro, trifluoromethyl and phenyl; with the proviso that when R₁ is hydrogen or 1 to 4 carbon alkyl, R₂ is not phenyl; and their 16, 17; 18, 19; 28, 29-hexahydro and 27-demethoxy-27-hydroxy analogous compounds.

2. A compound of claim 1 wherein: R₁ is selected from hydrogen, methyl, ethyl, propyl, butyl, isobutyl, amyl, isoamyl, octyl, dodecyl, phenyl and benzyl; R₂ is selected from amyl; isoamyl; octyl; dodecyl; allyl; 2-isobutenyl; 2-pentenyl; phenyl; phenyl substituted with one to three groups each independently selected from C₁₋₄ lower alkyl, chloro, bromo, fluoro, nitro, methoxy, trifluoromethyl, amino, sulfo, fluorosulfonyl, methylsulfonyl and difluoromethylsulfonyl; phenoxyethyl; phenoxyethyl wherein the phenoxy group has one to three substituents each independently selected from bromo, chloro, amino and acetamino; cyclopentyl, cyclohexyl, cycloheptyl, cyclooctyl, cyclopentadecyl and adamantanyl; 4-biphenyl; 4-phenylbenzyl; a heterocyclic ring selected from pyridine, pyridine substituted with 1 to 2 groups each independently selected from methyl and nitro, N-methyl piperidine, pyrimidine, pyrimidine substituted with 1 to 2 groups each independently selected from methyl, hydroxy and nitro, pyridazine, pyridazine substituted with 1 to 2 groups each independently selected from amino, chloro, phenoxy, piperidino, N-methyl-piperazino and bis-(hydroxyethyl)amino, quinoline, quinoline substituted with 1 to 2 groups each independently selected from methyl, methoxy, fluoro, trifluoromethyl and phenyl; with the proviso that when $R_1$ is hydrogen or 1 to 4 carbon alkyl, $R_2$ may not be phenyl; and their 16, 17; 18, 19; 28, 29-hexahydro and 27-demethoxy-27-hydroxy analogous compounds.

3. A compound of claim 1 which is the 2,4-dinitrophenylhydrazone of 3-formylrifamycin SV.

4. A compound of claim 1 which is the cyclopentadecylhydrazone of 3-formylrifamycin SV.

5. A compound of claim 1 which is the cyclooctylhydrazone of 3-formylrifamycin SV.

6. A compound of claim 1 which is diamylhydrazone of 3-formylrifamycin SV.

7. A compound of claim 1 which is the diphenylhydrazone of 3-formylrifamycin SV.

8. A compound of claim 1 which is the N-phenyl-N-benzylhydrazone of 3-formylrifamycin SV.

9. A compound of claim 1 which is the 3,4,6-trichlorophenylhydrazone of 3-formylrifamycin SV.

10. A compound of claim 1 which is the (1-adamantanyl)hydrazone of 3-formylrifamycin SV.

11. A compound of claim 1 which is the N-methyl-N-(4-phenylbenzyl)hydrazone of 3-formylrifamycin SV.

* * * * *